United States Patent [19]
Krongauz et al.

[11] Patent Number: 5,905,148
[45] Date of Patent: May 18, 1999

[54] PHOTOCHROMIC SPIROOXAZINE POLYSILOXANES

[75] Inventors: Valeri Krongauz; Alexander Zelichonok, both of Rehovot; Frida Buchholz, Rishon LeZion; Judith Ratner, Rehovot, all of Israel

[73] Assignee: Yeda Research and Development Co. Ltd., Rehovot, Israel

[21] Appl. No.: 08/906,974

[22] Filed: Aug. 6, 1997

[30] Foreign Application Priority Data

Dec. 8, 1996 [IL] Israel ......................................... 119781

[51] Int. Cl.$^6$ .............................. C07F 7/08; C07F 7/10; C07F 7/18
[52] U.S. Cl. .............................. 544/69; 544/71; 252/586; 351/163; 359/241; 359/242; 430/340
[58] Field of Search ........................ 544/69, 71; 252/586; 351/13; 359/241, 242; 430/340

[56] References Cited

U.S. PATENT DOCUMENTS

| | | | |
|---|---|---|---|
| 4,952,619 | 8/1990 | Greco et al. ............................... | 524/96 |
| 4,977,259 | 12/1990 | Greco et al. ............................... | 544/69 |
| 5,322,945 | 6/1994 | Krongauz et al. ......................... | 544/69 |
| 5,641,884 | 6/1997 | Utsunomiya et al. ..................... | 544/71 |

OTHER PUBLICATIONS

Crano, J.C. et al., "Spiroxazines and their use in photochromic lenses.", Applied Photochromic Polymer Systems, pp. 31–79 (1992).

Krongauz, V., "Photochromic liquid crystal polymers.", Applied Photochromic Polymer System, pp. 121–173 (1992).

Krongauz, V., "Environmental effects on organic photochromic systems.", chp. 21, pp. 793–821 (1990).

*Primary Examiner*—Richard L. Raymond
*Attorney, Agent, or Firm*—Browdy and Neimark

[57] ABSTRACT

Polysiloxane copolymers containing both photochromic and lightstabilizing groups with enhanced UV-fatigue resistance can be used as coatings for devices with variable optical density, including lenses, glazing, textiles and the like, to provide light-sensitive darkening effects. The photochromic groups are spironaphtooxazine groups and the lightstabilizing groups are hindered amine light stabilizing (HALS) groups.

15 Claims, 10 Drawing Sheets

TIME OF IRRADIATION (min.)

FIG. 9

PHOTOCHROMIC SPIROOXAZINE POLYSILOXANES

FIELD OF THE INVENTION

The present invention relates to photochromic compounds and more specifically to polysiloxane copolymers containing both photochromic and lightstabilizing groups with enhanced UV-fatigue resistance, which can be used as coatings for devices with variable optical density, including lenses, glazing, textiles and the like to provide light-sensitive darkening effects.

BACKGROUND OF THE INVENTION

Photochromic polymers, that is, polymers which contain photochromic groups in a macromolecule, are materials of significant technological potential in many industrial fields. For example, such polymers can be used in the manufacture of the plastic material of eye lenses and the manufacture of windows for the automobile industry.

Spirooxazines and their use in photochromic lenses have been recently reviewed by Crano et al., 1992. There has also been a significant amount of research reported on a number of side-chain photochromic polymers in which photochromic spiropyran or spirooxazine side groups are attached to a main chain through a flexible spacer (Krongauz, 1990, 1992). The structure of these compounds allows incorporation of a very high content of a photochrome in a polymer which can reach 100%. That is, each structural unit of the polymer contains the photochromic group. Properties of such polymers can be substantially different from the properties of the polymers containing photochromic molecules as solute, as photochromic compounds have been usually employed in photochromic lenses. Such solutions in polymers have inherent restrictions in solubility of the photochromic compound.

U.S. Pat. No. 5,322,945 (Krongauz et al.), assigned to the present applicants, describes spirooxazine photochromic polysiloxanes having an advantage over other spirooxazine photochromic compounds by giving high quality coatings for plastic lenses. However, these photochromic polysiloxane coatings exhibit rather low fatigue resistance against illumination with light.

European Patent EP 162524 describes organic polymer stabilizing compounds, which are derivatives of 2,2,6,6-tetramethylpiperidine, 2,2,6,6-tetramethylmorpholine or of 2,2,3,5,5-pentamethylpyrrolidine carrying a silyl group, which is capable of being hydrolyzed to silanol and is bonded to the ring structure by an Si—C bond. These compounds contain a sterically-hindered amino group together with a hydrolyzable silyl group, and are said to be able to stabilize organic polymers in general, and in particular homopolymers and copolymers of olefins and diolefins, such as polypropylene, polybutadiene and polyethylene of high and low density, especially towards ultraviolet radiation.

The reactive stabilizing compounds can give rise to resinification reactions, or can be anchored to a support or to the polymer to be stabilized, these characteristics enhancing the permanence of the stabilizer in the polymer.

The present inventors have tried to add the stabilizing compounds described in EP 162524 to photochromic polysiloxanes, particularly those described in U.S. Pat. No. 5,322,945. However, the maximum amount of such stabilizing compounds that could be added to the photochromic polysiloxanes without phase separation was less than 1% in relation to the polysiloxanes, such mixtures not giving any detectable protection against fatigue.

It would be highly desirable to provide new photochromic polysiloxane polymers that give high quality coatings for plastic lenses and give a significant protection against fatigue produced by light.

SUMMARY OF THE INVENTION

In accordance with the present invention, photochromic polysiloxane copolymers have been produced that contain both photochromic spironaphthooxazine and hindered amine light stabilizing (HALS) groups incorporated in polysiloxanes through a hydrocarbon spacer. These HALS groups include radicals derived from 2,2,6,6-tetramethylpiperidine, 2,2,6,6-tetramethylmorpholine and 2,2,3,5,5-pentamethylpyrrolidine. Other side groups required for promoting the polymer synthesis and/or improving physical and chemical properties of the polymers (viscosity, curing ability, etc.) may also be introduced into the copolymers.

The present invention thus provides a photochromic polysiloxane including functional moieties of the formula:

and optionally moieties of the formula:

wherein R″ is a $C_1$–$C_{15}$ alkyl; R‴ is H, OH, $C_3$–$C_{15}$ alkyl, or $C_3$–$C_{15}$ alkyl substituted by $C_1$–$C_2$ alkoxy, phenyl, naphthyl and phenyl substituted by one or more $C_1$–$C_4$ alkyl and/or OH; G is a photochromic radical derived from a compound wherein said compound is a photochromic compound of the formula I:

wherein $R_1$ is selected from the group consisting of (A) hydrogen, $C_1$–$C_6$ alkyl, phenyl, or $C_1$–$C_6$ alkyl substituted by halogen, hydroxy, methoxy, carboxyl, methoxycarbonyl, phenyl or diphenyl; and (B) —$(CH_2—)n—CH=CH_2$ wherein n is an integer from 1 to 20; when $R_1$ is (B), then $R_2$ through $R_8$ are each selected from the group consisting of hydrogen, $C_1$–$C_6$ alkyl, methoxy, hydroxy, phenyl, phenyl-carbonyloxy, phenyl($C_1$–$C_6$)alkyl carbonyloxy, di($C_1$–$C_6$)alkylamino, ($C_1$–$C_6$)alkylphenylamino, piperidino, indolino and tetrahydroquinolino; when $R_1$ is (A), then one of $R_2$ through $R_8$ are (C)—X—($CH_2$—)n—CH=$CH_2$, wherein n is an integer from 1 to 20 and X is selected from the group consisting of a covalent bond, O, N—R' (wherein R' is H or $C_1$–$C_6$ alkyl), CO—O, CO—NH, and —CH=N and the remaining ones of $R_2$ through $R_8$ are selected from the group consisting of hydrogen, $C_1$–$C_6$ alkyl, methoxy, hydroxy, phenyl, phenylcarbonyloxy, phenyl($C_1$–$C_6$)alkyl carbonyloxy, di($C_1$–$C_6$)alkylamino, ($C_1$–$C_6$) alkylphenylamino, piperidino, indolino and tetrahydroquinolino, said radical ($CH_2$)$_{\overline{n+2}}$G being covalently bonded through the alkene carbon of radical $R_1$ as moiety (B) or of $R_2$ through $R_8$ as moiety (C); and U is a radical derived from a compound selected from a compound of the formulas II–IV herein:

where m is an integer from 1 to 20, said radical ($CH_2$)$_{\overline{m+2}}$U being covalently bonded through the alkene carbon atom; and the polysiloxanes being cyclic or linear including terminal groups of the formulas (R")$_3$—Si—, covalently bonded to the Si atom of an [Si—O] moiety and Si—(R")$_3$ covalently bonded to the O atom of an [Si—O] moiety. R" is preferably methyl and R"' is preferably $C_3$–$C_7$ alkyl, more preferably heptyl, or $C_3$–$C_4$ alkyl substituted by phenyl substituted by one or more $C_1$–$C_4$ alkyl and/or OH, more preferably a 4-hydroxy-3,4-di(t-butyl)phenyl radical. The invention further provides coated articles, particularly coated lenses, comprising a substrate, e.g., a lens substrate, coated with a photochromic polysiloxane of the invention. The copolymers and their blends are coated on the plastic lens surface and the film is cured by heating. A second scratch resistance layer can be coated to improve mechanical properties of the film and can also be cured by heating. The photochromic properties of the films, especially photofatigue resistance of the photochromic copolymers are substantially better than those of the films based on the polymers that do not include the HALS group.

BRIEF DESCRIPTION OF THE FIGURES

Other advantages of the present invention will be readily appreciated as the same becomes better understood by reference to the following detailed description when considered in connection with the accompanying drawings wherein:

FIGS. 5A and 5B show spectra of the polysiloxane copolymer prepared from spironapthooxazine Ia/HALS II, ratio 1:1, according to Example 1, irradiated with UV light at different stages of thermal color decay. The spectra were recorded at 1 min intervals: (FIG. 5A) The non-cured film ($\tau_{1/2}$=1.5 min); (FIG. 5B) The film cured by heating at 85° C. during 1 hr ($\tau_{1/2}$=12 min) (Example 6) (t=+27° C.).

DETAILED DESCRIPTION OF THE INVENTION

The present invention provides photochromic polysiloxane copolymers including siloxane functional moieties having both a photochromic monomer and a light stabilizer of the hindered amine type, herein referred to as a HALS monomer, covalently bound thereto.

The photochromic monomers used in the present invention are those of the general formula (I) herein. Some of them have been described in U.S. Pat. No. 5,322,945, herein incorporated in its entirety by reference.

The above-described photochromic monomer of formula I is characterized by including a linker arm selected from (B) —(CH$_2$—)n—CH=CH$_2$ extending from the indoline nitrogen as the R$_1$ group, and (C) —X—(CH$_2$—)n—CH=CH$_2$ when the linker arm extends from a phenyl carbon as in groups R$_4$ to R$_8$ or an indoline carbon as in groups R$_2$ and R$_3$.

The chemical differences between these two groups are due to the nature of the synthetic reactions used to assemble the photochromic compound as discussed below. In either case, an alkene linker arm extends from either the indole nitrogen or carbon or a phenyl carbon, the linker arm having a length of 3 to 22 carbons.

The number of carbons in the linker arm is significant with regard to the efficiency of the addition reaction to the polymer as it is known in the art.

Each photochromic monomer includes a single linker arm as groups R$_1$ through R$_8$, the remaining groups being various functionalities as defined above. These functionalities can be synthesized by chemical reactions known in the art, for example as described in U.S. Pat. No. 5,322,945 and in Crano et al., 1992.

wherein in formulas Ib and Ic, R$_1$, R$_4$ and R$_5$ are H or lower alkyl, preferably methyl.

The compound of formula Ia has been described in U.S. Pat. No. 5,322,945. The compounds Ib and Ic are novel monomers and are part of the present invention.

HALS monomers used in the present invention are the derivatives of 2,2,6,6-tetramethylpiperidine, 2,2,6,6-tetramethylmorpholine and 2,2,3,5,5-pentamethylpyrrolidine of formulas II, III and IV herein, respectively. The preparation of these compounds is described in EP 162524.

In one embodiment, the invention comprises a random linear polysiloxane of the formula:

Examples of photochromic monomers used in the present invention are those of formulas Ia, Ib and Ic as follows:

wherein x, y and z are integers, the sum of which k is an integer of at least 4, x can be equal to zero, and n and m are integers of 1 through 20, and R", R'", G and U are as defined before. In one example, k is 80, y and z being 39 and x=2, n=4 and m=3.

In another embodiment, the invention provides a cyclic polysiloxane having the formula:

wherein k, x, y, z, n, m, R", R'", G and U are as defined above. In one example, k is 4.

The values of k=x+y+z are inherent properties derived from commercially available siloxane polymers. Hence, since the values of k are not at all rate limiting on the synthetic reactions of the invention and there is no relative limit on the values of k as conventional siloxane polymers are derived, the only limitation is their lower value and that they are integers.

The invention further relates to a method for the preparation of the fatigue resistant photochromic polysiloxane copolymers of the invention containing both spironaphthooxazine photochromic groups and HALS groups connected to the main chain through a flexible alkyl linker arm, which comprises adding a photochromic spironaphthooxazine monomer of formula I herein containing an alkene terminated side-chain and a HALS monomer including an alkene terminated side-chain of formula II, III or IV herein to an Si—H-containing polymer, wherein the photochromic spironaphthooxazine and HALS groups will bind covalently through the alkene carbon to [SiH] moieties of the siloxane polymer. The reaction is preferably carried out in the presence of a metal-containing catalyst, most preferably a Pt-containing catalyst. The reaction proceeds to a high degree of completion of about 100% substitution.

An advantage of the polysiloxane copolymers of the present invention as compared, for example, to the prior art polysiloxanes described in U.S. Pat. No. 5,322,945 is a very high protection of the photochromic groups from UV irradiation degradation due to the statistical distribution of the spironaphthooxazine and HALS side groups in the macromolecule, thus imparting substantially higher photochromic stability to the polysiloxane polymers.

Even at a high concentration of the HALS groups there is no phase separation and they are in very close proximity to the photochromic groups. The polymers can be easily cured on a polymer surface by mild heating, forming a transparent film, whose rigidity depends on a relative content of different side groups in a macromolecule, which also strongly affects the kinetics of the photochromic reactions.

EXPERIMENTAL SECTION

The invention will now be illustrated by the following examples, to which it is not limited.

In these examples, the following chemicals were used without further purification: 2,3,3-trimethylindoline (Aldrich), allyl iodide (BDH), 6-bromo-1-hexene (Fluka), 1-nitroso-2-naphthol, 98% (Aldrich), 2,2,6,6-tetramethyl-4-piperidinol, 98% (Aldrich), 1,2-naphthoquinone-4-sulfonic acid potassium salt, 90% (Aldrich), piperidine (BDH). The polymers used are: poly(methylhydrosiloxane), degree of polymerization (DP)=35 (Merck) and DP=80 (ABCR), tetra- and penta(methylhydrosiloxane) (ABCR).

Example 1.

Figure 1:
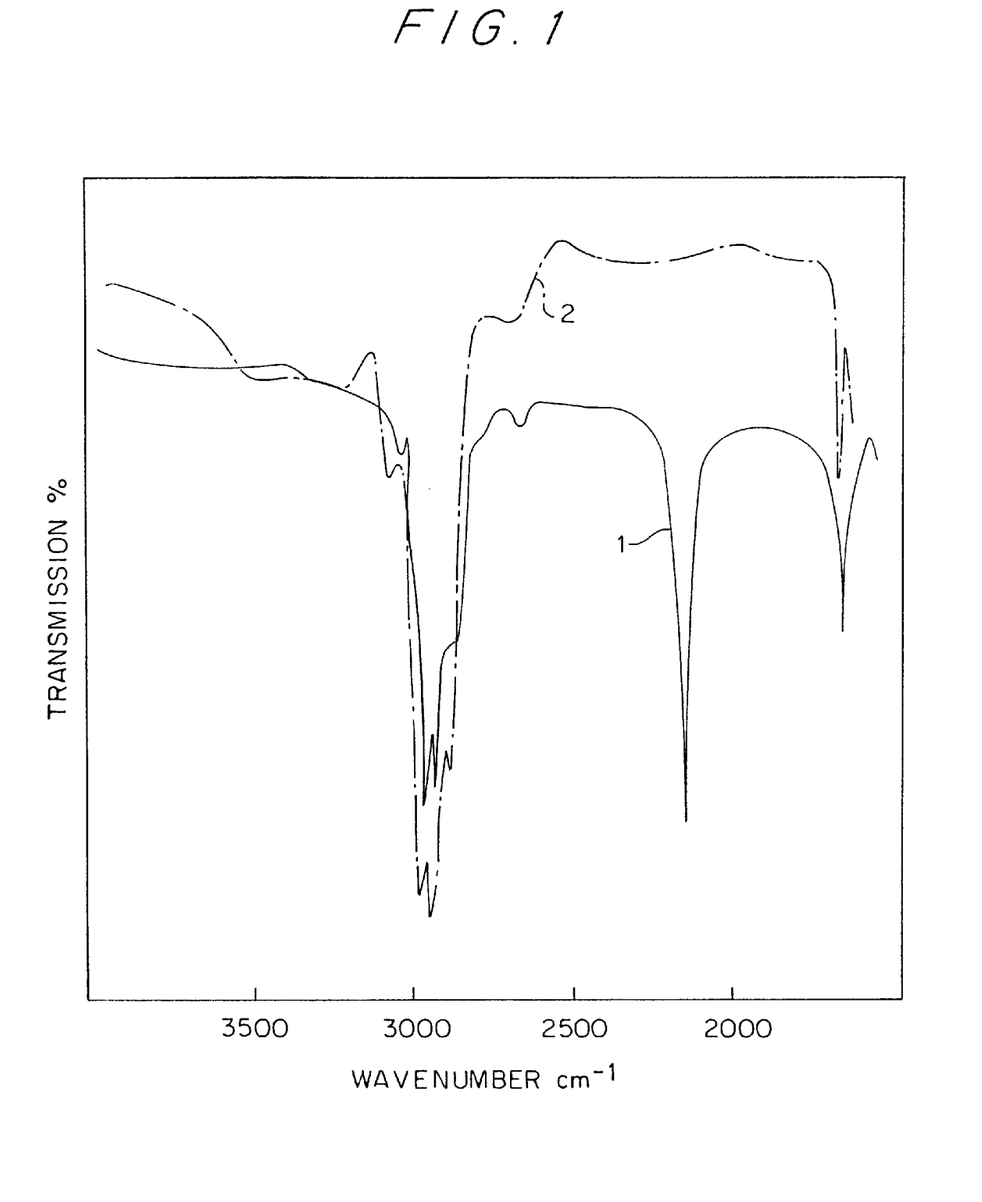
FIG. 1 shows infrared (IR) spectra of the initial reaction mixture (curve 1) and of the linear copolymer (curve 2) prepared from spironaphthooxazine (compound Ia ) and HALS (compound (II), ration 1:1, according to Example 1, obtained after 36 h heating at 80° C.; the Si—H absorption band at 2140 $cm^{-1}$ disappears.

*Preparation of Photochromic Linear Polysiloxane Copolymers with Spironaphthooxazine and Tetramethylpiperidine Side Groups.* 300 ml (0.76 mmol) of the spironaphthooxazine derivative (compound Ia, n=4), 150 mg (0.76 mmol) of the tetramethylpiperidine derivative (compound II, n=1) and 92 mg (1.52 mmol) of linear poly (methylhydrosiloxane), DP=80 (ABCR) and 0.23 mg of $Pt(C_{10}H_{12})Cl_2$ were dissolved in dry toluene. The flask was sealed and kept for 36 hours at 80° C. until the Si-H absorption band at 2140 $cm^{-1}$ had practically disappeared (FIG. 1). The polymer was precipitated by methanol and freeze-dried from benzene under high vacuum. Analysis of the UV-visible electronic spectra of the copolymer, according to Zelichenok et al. *Macromolecules* 25, 3179–3183 (1992) indicates that the copolymer contains photochromic and HALS groups in a ratio of 1:1 (not shown).

The spironaphthooxazine compound Ia was prepared as described in U.S. Pat. No. 5,322,945 and the tetramethylpiperidine compound II was prepared as described in EP 162524.

Figure 2:
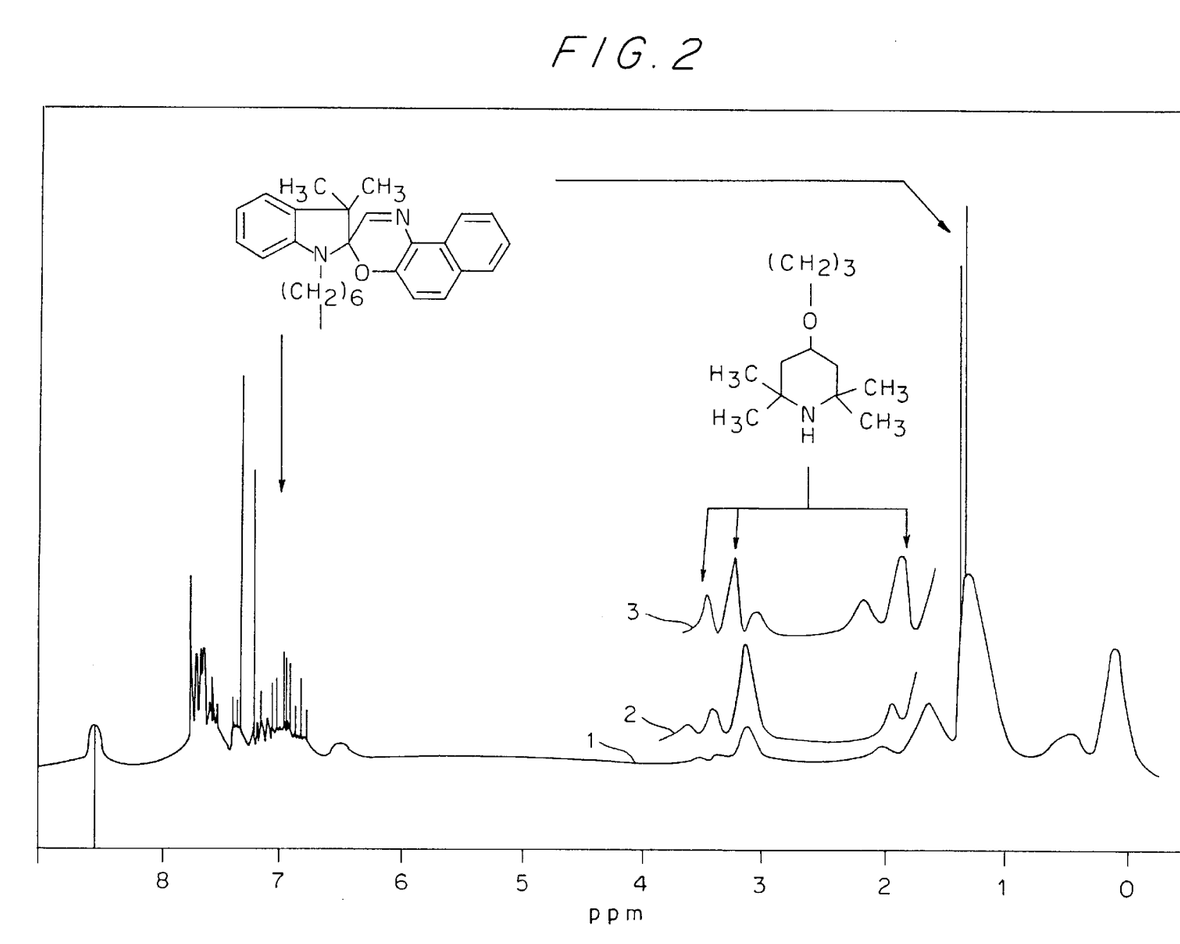
FIG. 2. shows NMR spectra of the copolymers prepared from the feeds according to Example 1 with different spironapthooxazine (compound Ia)/HALS (compound II) ratios: (1) 9:1; (2) 7:3; (3) 1:1. The integration indicates a proportional increase of the HALS concentration in the copolymers.

The same procedure was applied for the preparation of copolymers with other relative contents of the spironaphthooxazine Ia and HALS II side groups (9:1 and 7:3). Analysis of the UV-visible electronic spectra of the copolymers indicated that the ratio of spironaphthooxazine/HALS side groups in the copolymers coincides with the corresponding monomers in the feed (not shown). This is also illustrated in FIG. 2 by the NMR spectra of the three copolymers prepared from the feeds with 9:1 (curve 1), 7:3 (curve 2) and 1:1 (curve 3) spironaphthooxazine/HALS ratios.

A similar procedure was used for preparing copolymers containing other spironaphthooxazine side groups, for example, copolymers containing the 6'-piperidino-substituted spironaphthooxazine compound of formula Ib herein and the HALS monomer II, ration 1:1. The synthesis of the novel compound Ia is described in Example 4 herein.

Example 2.

Figure 3:
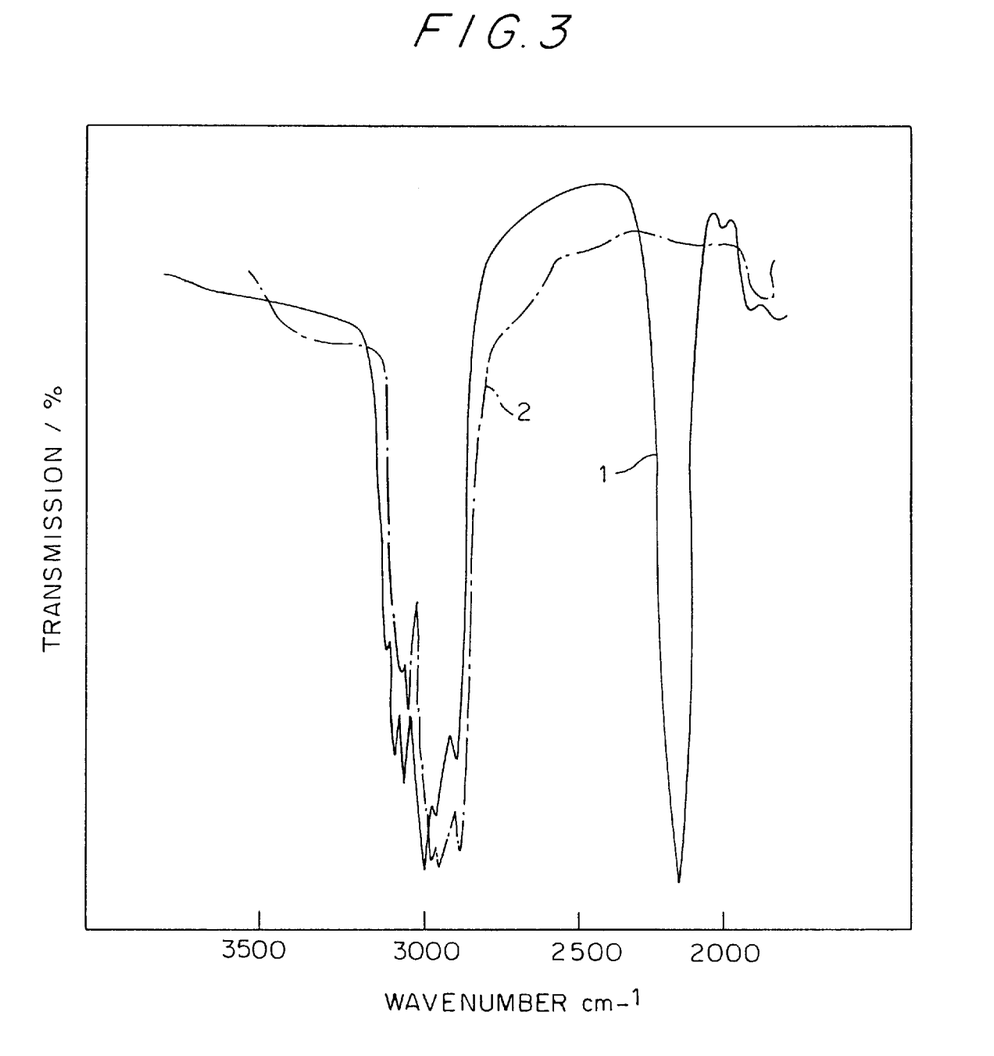
FIG. 3 shows IR spectra of the initial reaction mixture (1) and of the linear triple polysiloxane copolymer (2) obtained from spironaphthooxazine Ia, HALS II and heptene, ratio 6:3:1, according to Example 2, after completion of the reaction (36 h, heating 80° C.).
Figure 4:
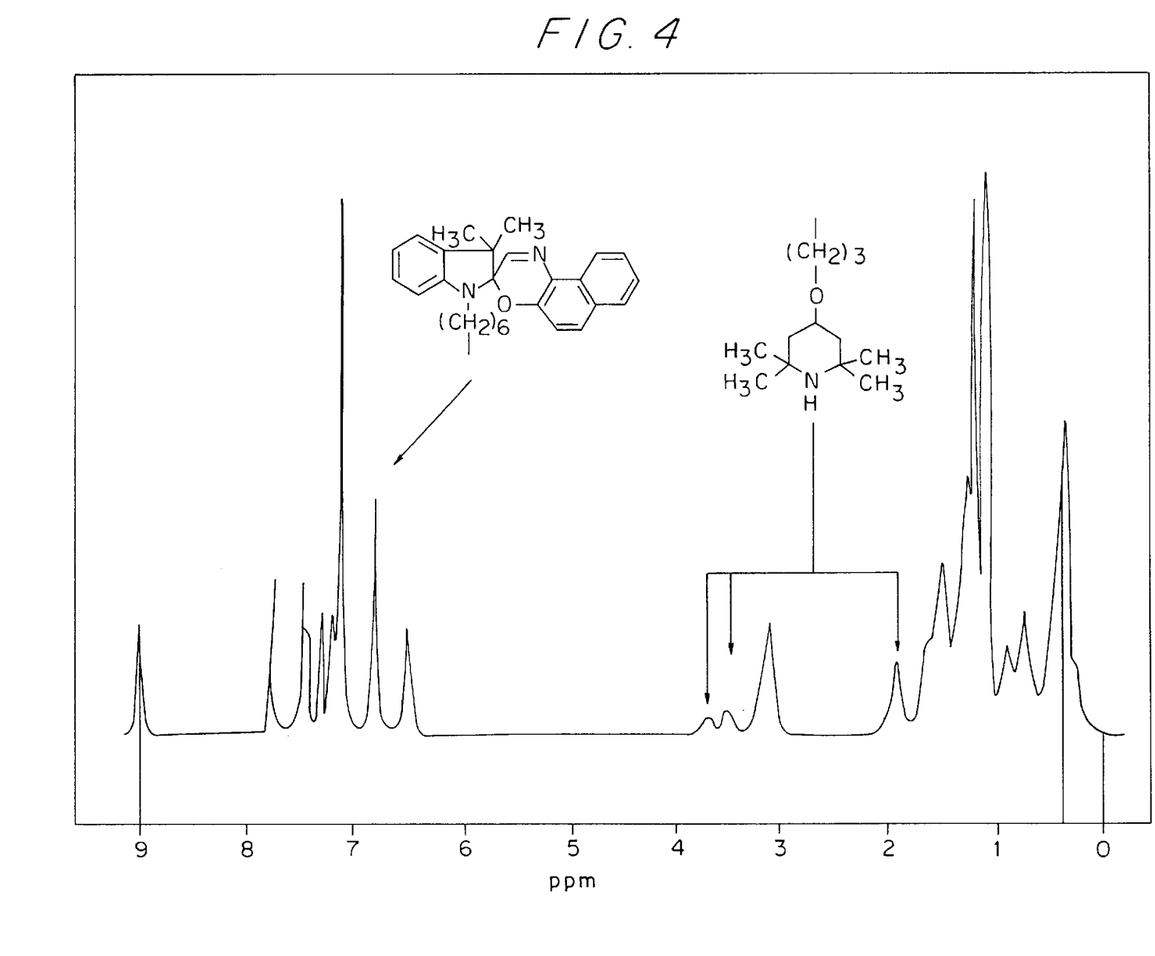
FIG. 4 shows NMR spectrum of the triple polysiloxane copolymer according to Example 2, prepared from spironaphthooxazine Ia, HALS II and heptene, ratio 6:3:1.

*Preparation of Photochromic Linear Polysiloxane Triple Copolymers with Spironaphthooxazine, Tetramethylpiperidine and Heptane Side Groups.* 500 mg (1.26 mmol) of spironaphthooxazine derivative (compound Ia, n=4), 124 mg (0.63 mmol) of HALS (compound II, n=1), 21 mg (0.21 mmol) of heptene, 126 mg (2.1 mmol) of linear poly (methylhydrosiloxane), DP=80 (ABCR), and 0.35 mg $Pt(C_{10}H_{12})Cl_2$ were treated as described in Example 1. Completion of the reaction is shown by IR and NMR spectra depicted in FIGS. 3 and 4, respectively. The spirooxazine Ia/HALS II/heptane ratio in the copolymer was 6:3:1, as it was in the feed. Other R'" side groups, such as alkyl substituted by aryl or alkoxy etc. can be incorporated in the polysiloxane copolymers in a similar way.

By the same procedure, a triple polysiloxane copolymer was prepared from spironaphthooxazine compound Ib, HALS II and heptene, in the ratio 6:3:1.

Example 3.

*Preparation of Photochromic Cyclic Copolymer* (K=40). 150 mg (0.38 mmol) of the spironaphthooxazine derivative (compound Ia, n=4), 74.9 mg (0.38 mmol) of HALS (compound II), ratio 1:1, 33.5 (0.76 mmol) of tetra (methylhydrosiloxane) and 0.12 mg of $Pt(C_{10}H_{12})Cl_2$ were treated as described in Example 1, thus producing the cyclic copolymer.

Example 4.

*Preparation of 1-(1-Hex-5-Enyl)-3,3-Dimethyl-6"-Piperidinospiro-[Indoline-2.3"-3H-Naphtho[2,1-b] 1,4-Oxazine]* (Compound Ib). 2.38 g (0.099 mmol) of 4-piperidino-1,2-naphthoquinone was prepared by the same method as is known for the preparation of 4-morpholino-1, 2-naphthoquinone The product was then heated under reflux with 0.82 g, (0.119 mmol) hydroxylamine hydrochloride in the presence of a base. The solvent was removed and the residue was dissolved in methylenechloride, washed with brine and dried. The solvent was evaporated to yield 4-piperidino-1,2-naphthoquinone monooxime as an oil which was reacted with equal amounts of 1-(1-hex-5-enyl)-3,3-dimethyl-2-methylene indoline (prepared as described in U.S. Pat. No. 5,322,945) in boiling trichloroethylene. The solvent was removed and the resulting oil chromatographed on silica to give the pure product. $^1$H NMR (400 MHz, $C_6D_6$)δ: 0.93(s,6H); 1.17–1.68 (m, 10H); 1.86–1.92 (m, 2H (C$\underline{H}_2$—CH:CH$_2$)); 2.80 (broad s, 4H, N(CH$_2$)$_2$)); 3.14 (m, 2H (—N—C$\underline{H}_2$—)); 4.98 (m, 2H (H$_2$$\underline{C}$=CH—)); 5.70 (m, 1H (H$_2$C=C$\underline{H}$—)); 6.55 (d, 1H); 6.59 (s, 1H); 6.93 (t, 1H); 7.00 (m, 1H); 7.19 (m, 1H); 7.36 (dt, 1H); 7.54 (dt, 1H); 7.69 (m, 1H); 8.28 (d, 1H); 9.20 (d, 1H).

Example 5.

*Coating of the Plastic Lens Surface With Light-Stabilized Photochromic Polysiloxane Copolymers of the Invention.*

A 50% toluene solution of the polysiloxane triple copolymer of Example 2 containing 60% of the spironaphthooxazine Ia groups, 30% of the HALS II groups and 10% of heptane was used for plastic (CR-39) lens coating. The lenses were coated by dipping or spinning. After drying, the lenses were heated over 45–60 min. at 85° C., which led to a marked hardening of the copolymer film, as a result of curing the polymer.

For additional improved mechanical properties of the films, they were coated with a layer of a scratch-resistant coating (Rupp and Hubrach), without any marked change in transparency being observed.

Example 6.

*Spectra and Color Decay Kinetics.*

Figure 5A:
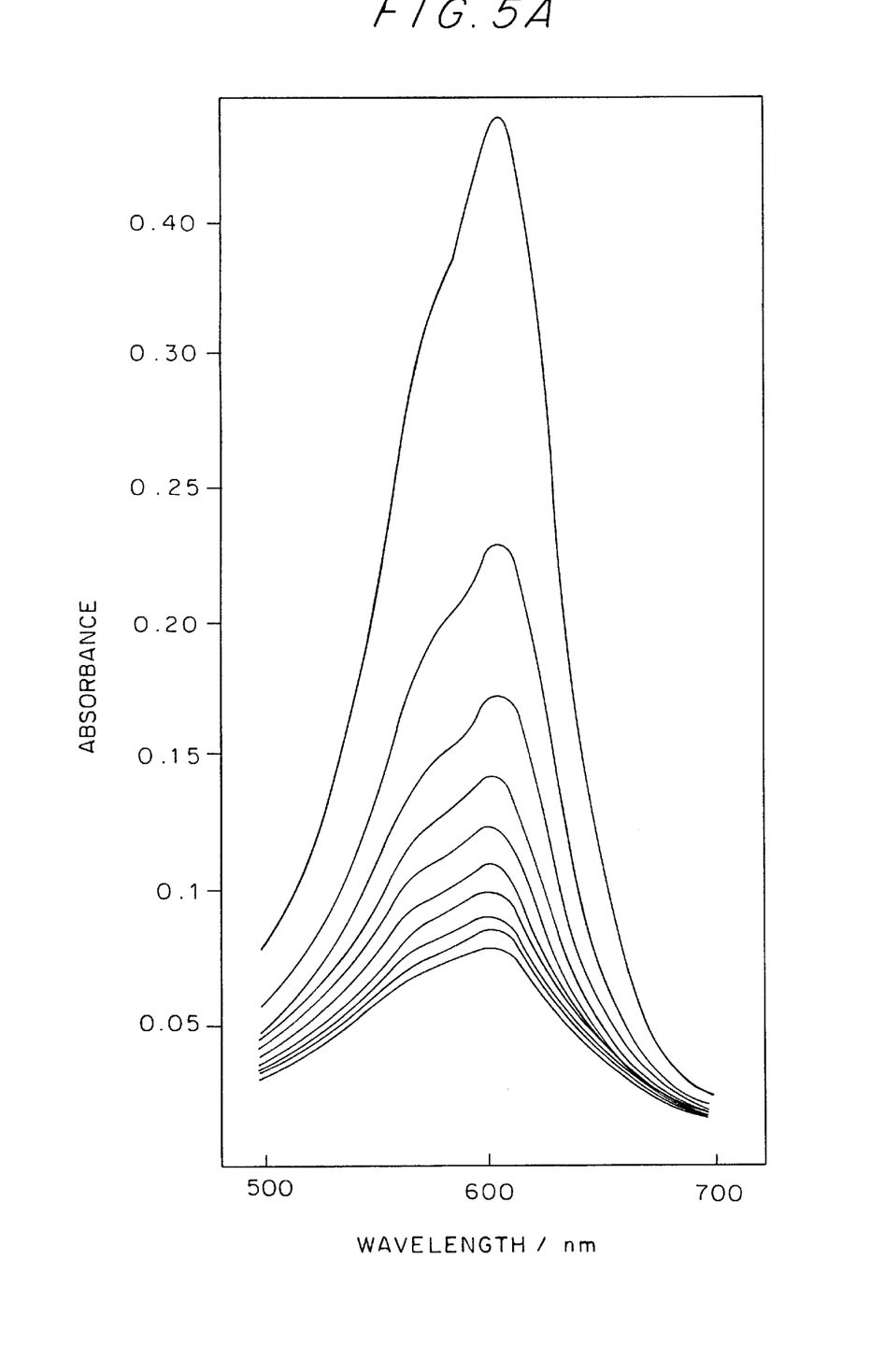
Figure 5B:
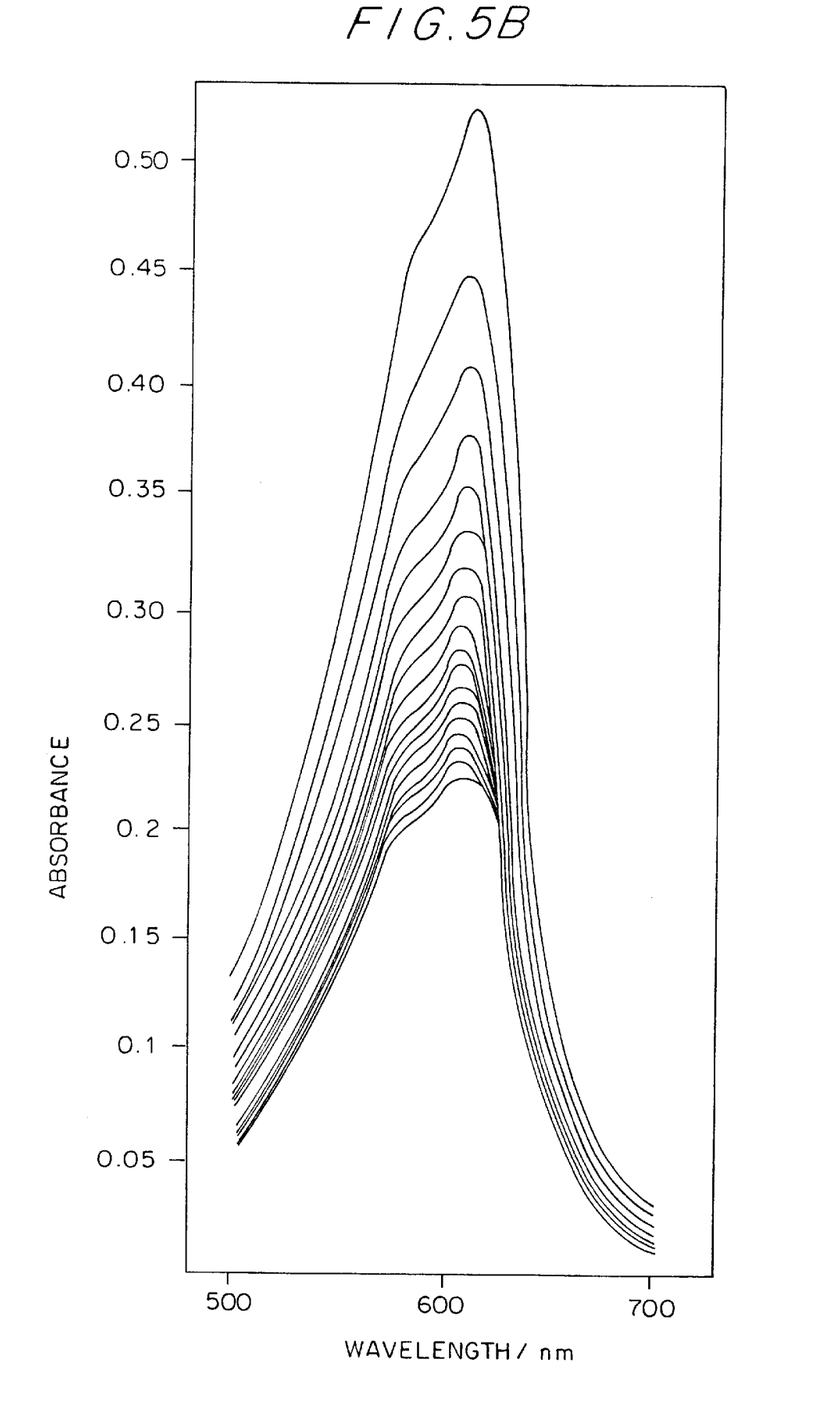
Figure 6:
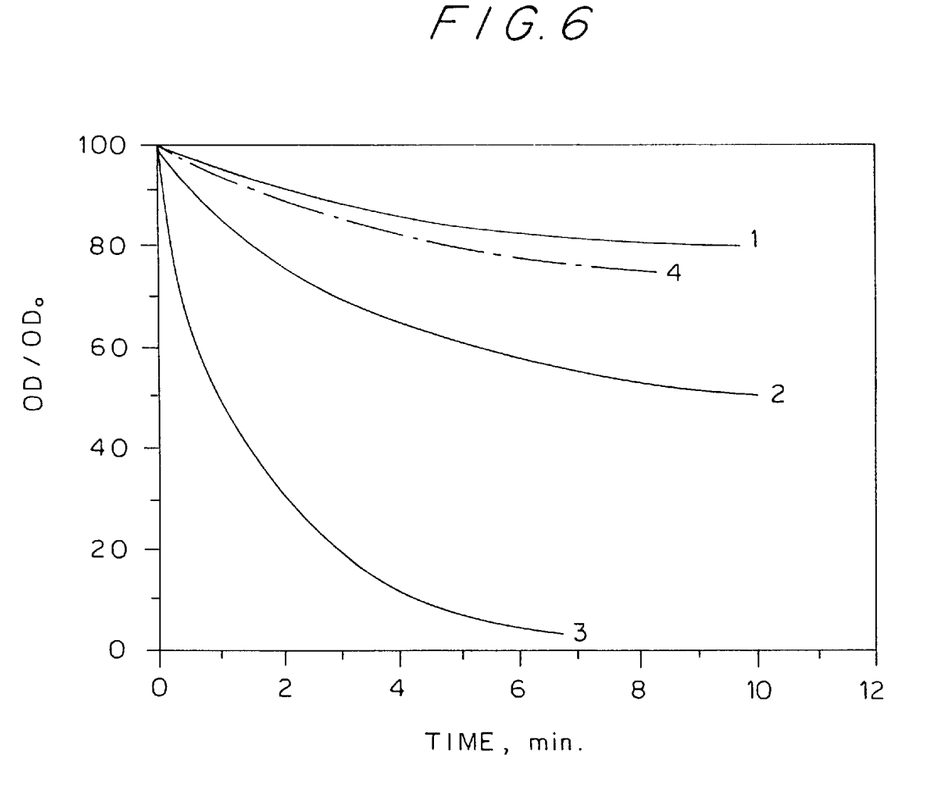
FIG. 6 shows kinetics of the color decay of UV-irradiated films of the photochromic polysiloxanes of Example 1 with the following copolymer compositions: spironapthooxazine Ia HALS II: (1) 9:1 ($\tau_{1/2}$>30 min); (2) 7:3 ($\tau_{1/2}$=10 min); (3) 1:1 ($\tau_{1/2}$=1.5 min). The curve (4) relates to the triple spironaphthooxazine Ia/HALS II/heptane copolymer 6:3:1 of Example 2 ($\tau_{1/2}$>30 min) (Example 6) (t=+27° C.).
Figure 7:
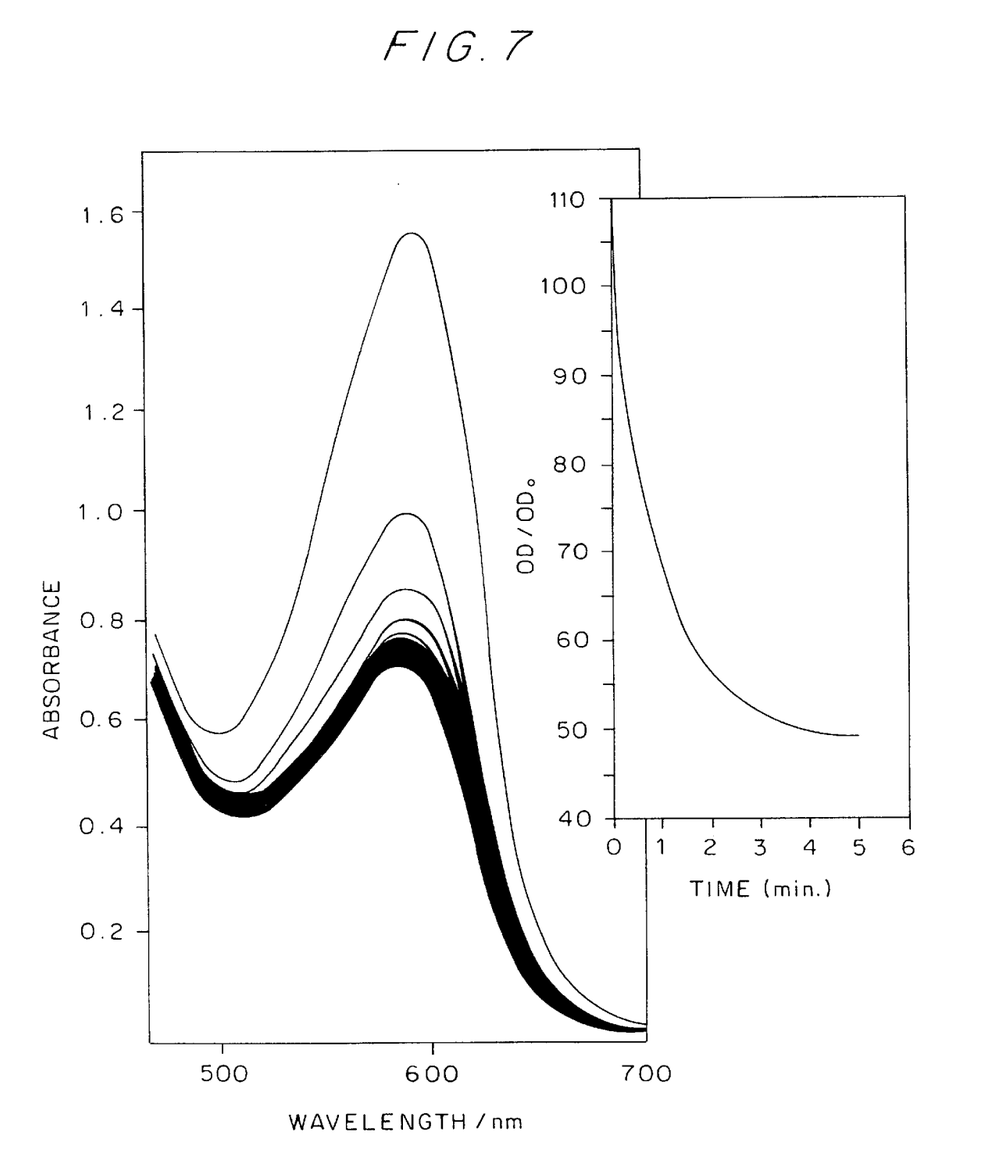
FIG. 7 shows spectra and color decay of UV-irradiated films of the triple polysiloxane copolymer prepared from spironaphthooxazine (compound Ib)/ HALS II/heptane, ratio 6:3:1, according to Example 2 ($\tau_{1/2}$=3.5 min) (t=+10° C.).

The absorption spectra of UV-irradiated light-stabilized photochromic polysiloxanes containing spironaphthooxazine Ia and Hals II, according to Example 1, ratio 1:1, in the films, are shown in FIGS. 5A and 5B. The typical kinetics of decoloration processes of UV-irradiated films of copolymers according to Examples 1 and 2, as shown in FIGS. 6 and 7, indicate that the higher the HALS content, the faster the decay. The color-decay does not obey first-order kinetics. The initial fast decay is followed by a slower one. As a first approximation, the color decay can be described by a sum of two exponential equations with fast and slow rate constants. Therefore, for comparison of different samples, the half-life time parameter ($\tau_{1/2}$) was used.

Example 7.

*Photostability of the Copolymers.*

Figure 8:
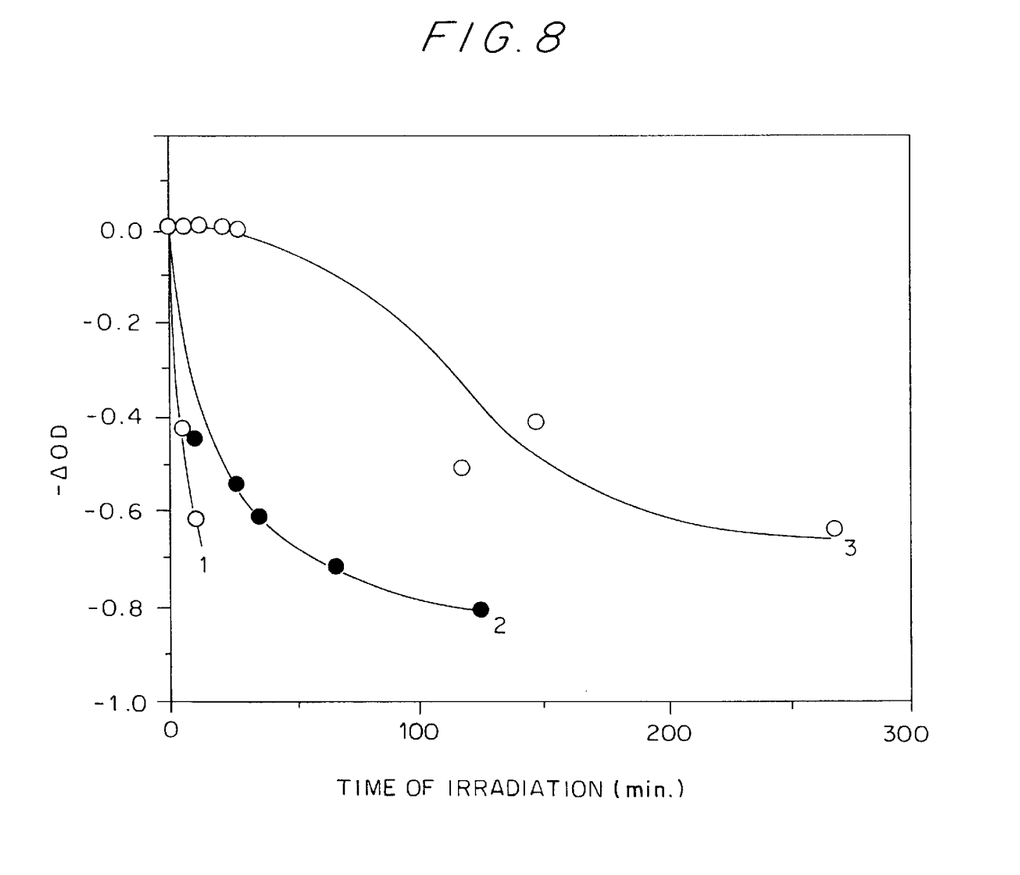
FIG. 8 shows change of the steady-state optical density of the copolymer films after irradiation with non-filtered light of a medium pressure mercury lamp. (1) Polysiloxane homopolymer with 100% spirooxazine (compound Ia) substitution; (2) Copolymer spironaphthooxazine Ia/heptane, 6:4; (3) Copolymer spironaphthooxazine Ia/HALS II/heptane, 6:3:1 of Example 2.
Figure 9:
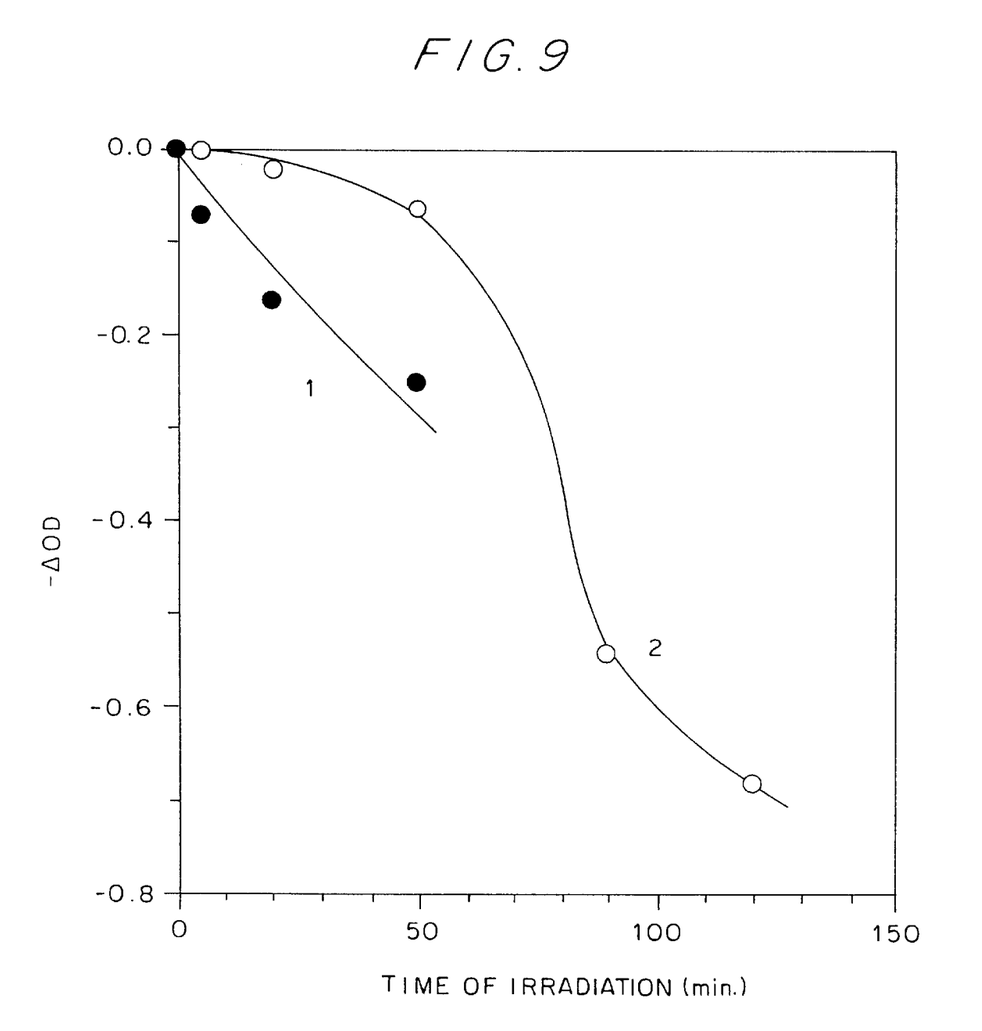
FIG. 9 shows change of the steady-state optical density of photochromic copolymers with spironaphthooxazine (compound Ib) after irradiation with nonfiltered light of a medium pressure mercury lamp. (1) Polysiloxane copolymer spironaphthooxazine Ib/heptane, 6:4; (2) Copolymer spironaphthooxazine Ib/ HALS II/heptane, 6:3:1 of Example 2.

Incorporation of HALS groups by covalent bonds in photochromic polysiloxanes results in a significant increase of photochemical stability of the copolymers. FIGS. 8 and 9 indicate that photo-induced fatigue of the copolymers is inhibited by incorporating the tetramethylpiperidino (HALS) groups into polysiloxane. The effect is increased with the HALS content in the copolymers.

The degradation curves, the change of optical density of color as a function of irradiation time, have different shapes for the copolymers with and without HALS groups. The latter have an induction period, which is clearer for the copolymers with a high HALS concentration.

This example demonstrates the possibility of enhancing photostability of photochromic polysiloxanes by incorporation into a macromolecule of both photochromic and light-stabilizing groups. Random distribution of the side groups in a macromolecule leads to very close proximity of these groups and efficient light protection.

References

1. Crano J. et al. (1992) in Applied Photochromic Polymer Systems, (C. B. McArdle, ed.), Blackie & Sons, Glasgow/London pp. 31–76.
2. Krongauz, V. et al. (1990) in Photochomism: Molecules and Systems, (H. Duer and H. Bonas-Laurent, eds.), Elsevier, pp. 793–821.
3. Krongauz, V. et al. (1992) in Applied Photochromic Polymer Systems, (C. B. McArdle, ed.), Blackie & Sons, Glasgow/London pp. 121–173.

We claim:

1. A photochromic light-stabilized polysiloxane including functional moieties of the formula and optionally moieties of the formula:

wherein R" is a $C_1$–$C_{15}$ alkyl; R'" is H, OH, $C_3$–$C_{15}$ alkyl, or $C_3$–$C_{15}$ alkyl substituted by $C_1$–$C_2$ alkoxy, phenyl, naphthyl and phenyl substituted by one or more $C_1$–$C_4$ alkyl and/or OH; G is a photochromic radical derived from a compound wherein said compound is a photochromic compound of the formula I:

wherein $R_1$ is selected from the group consisting of (A) hydrogen, $C_1$–$C_6$ alkyl, phenyl, or $C_1$–$C_6$ alkyl substituted hy halogen, hydroxy, methoxy, carboxyl, methoxycarbonyl, phenyl or diphenyl; and (B)—$(CH_2-)n$—$CH=CH_2$ wherein n is an integer from 1 to 20; when $R_1$ is (B), then $R_2$ through $R_8$ are each selected from the group consisting of hydrogen, $C_1$–$C_6$ alkyl, methoxy, hydroxy, phenyl, phenylcarbonyloxy, phenyl(C1–C6)alkyl carbonyloxy, di(C1–C6)alkylamino, (C1–C6)alkylphenylamino, piperidino, indolino and tetrahydroquinolino; when $R_1$ is (A), then one of $R_2$ through $R_8$ are (C) —X—$(CH_2-)n$—$CH=CH_2$, wherein n is an integer from 1 to 20 and X is selected from the group consisting of a covalent bond, O, N—R' (wherein R' is H or lower alkyl), CO—O, CO—NH, and —CH=N and the remaining ones of $R_2$ through $R_8$ are selected from the group consisting of hydrogen, $C_1$–$C_6$ alkyl, methoxy, hydroxy, phenyl, phenylcarbonyloxy, phenyl(C1–C6)alkyl carbonyloxy, di(C1–C6)alkylamino, (C1–C6)alkylphenylamino, piperidino, indolino and tetrahydroquinolino, said radical $(CH_2)_{\overline{n+2}}G$ being covalently bonded through the alkene carbon of radical $R_1$ as moiety (B) or of $R_2$ through $R_8$ as moiety (C); and U is a radical derived from a compound selected from a compound of the formulas II–IV herein:

(III)

(II)

(IV)

where m is an integer from 1 to 20, said radical $(CH_2)_{\overline{m+2}}U$ being covalently bonded through the alkene carbon atom; and the polysiloxanes being cyclic or linear including terminal groups of the formulas $(R")_3—Si—$, covalently bonded to the Si atom of an [Si—O] moiety and $Si—(R")_3$ covalently bonded to the O atom of an [Si—O] moiety.

2. A polysiloxane of claim 1 of the formula:

wherein x, y and z are integers, the sum of which k is an integer of at least 4, x can be equal to zero, and n and m are integers of 1 through 20, and R", R'", G and U are as defined in claim 1.

3. A polysiloxane of claim 2 wherein R" is $CH_3$, k=80, y=39, z=39, x=2, n=4, m=1, G is a radical and U is a radical

4. A polysiloxane of claim 2 wherein R'" is heptyl, x=8, y=48, z=24, n=4, m=1, G is a radical and U is a radical 5. A polysiloxane of claim 2 wherein G is a radical R'" is heptyl, U is as defined in claim 3, x=8, y=48, z=24, n=4 and m=1.

6. A polysiloxane of claim 1 of the formula wherein k=x+y+z is an integer of at least 4, G, U, R" and R'" are defined in claim 2.

7. A method for the preparation of a photochromic light-stabilized polysiloxane as defined in claim 1, which comprises reacting a poly(alkyl-hydrosiloxane) with a monomer derived from photochromic spironaphthooxazine compound I and a monomer derived from compound II, III or IV, wherein the radicals $(CH_2)_{\overline{n+2}}G$ derived from compound I and $(CH_2)_{\overline{m+2}}U$ derived from compounds II, III or IV, are linked covalently through the alkene carbon to [SiH] moieties of the polysiloxane, thus obtaining a polysiloxane as defined in claim 1 wherein R''' is H.

8. A coated article comprising:
   a substrate layer, and
   a coating layer consisting of a polysiloxane as defined in claim 1.

9. A coated article comprising:
   a substrate layer, and
   a coating layer consisting of a polysiloxane as defined in claim 2.

10. A coated article according to claim 8 further containing a coating layer with scratch-resistant properties.

11. A coated lens comprising:
    a lens substrate coated with a polysiloxane as set forth in claim 1.

12. A coated article comprising:
    a lens substrate coated with a polysiloxane as defined in claim 2.

13. A coated lens according to claim 11 further comprising a coating layer with scratch-resistant properties.

14. A method of producing a coated article according to claim 10 which comprises curing both the polysiloxane layer and the scratch-resistant layer by heating.

15. A method for the preparation of a photochromic light-stabilized polysiloxane as defined in claim 1, which comprises reacting a poly(alkyl-hydrosiloxane) with a monomer derived from photochromic spironaphthooxazine compound I; a monomer derived from compound II, III or IV; and an alkene monomer, wherein the radicals $(CH_2)_{\overline{n+2}}G$ derived from compound I and $(CH_2)_{\overline{m+2}}U$ derived from compounds II, III and IV, are linked covalently through the alkene carbon to moieties of the polysiloxane, thus obtaining said polysiloxane wherein R''' is alkyl.

* * * * *